(12) United States Patent
Boeing et al.

(10) Patent No.: US 8,859,834 B2
(45) Date of Patent: Oct. 14, 2014

(54) PROCESS FOR THE SELECTIVE HYDROGENATION OF MULTIPLY UNSATURATED HYDROCARBONS IN OLEFIN-CONTAINING HYDROCARBON MIXTURES

(75) Inventors: Christian Boeing, Cologne (DE); Markus Winterberg, Datteln (DE); Tobias Laiblin, Rosendahl (DE); Gunnar Schilling, Herten (DE); Wolfgang Garstka, Heiden (DE); Burkard Kreidler, Recklinghausen (DE); Dietrich Maschmeyer, Recklinghausen (DE); Reiner Bukohl, Marl (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 13/808,010

(22) PCT Filed: Jun. 9, 2011

(86) PCT No.: PCT/EP2011/059601
§ 371 (c)(1),
(2), (4) Date: Mar. 15, 2013

(87) PCT Pub. No.: WO2012/004081
PCT Pub. Date: Jan. 12, 2012

(65) Prior Publication Data
US 2013/0172641 A1    Jul. 4, 2013

(30) Foreign Application Priority Data
Jul. 6, 2010 (DE) .......................... 10 2010 030 990

(51) Int. Cl.
*C07C 5/00* (2006.01)
*C07C 7/163* (2006.01)
*C10G 45/40* (2006.01)
*C07C 5/05* (2006.01)
*C10G 45/32* (2006.01)

(52) U.S. Cl.
CPC . *C07C 5/05* (2013.01); *C07C 7/163* (2013.01); *C10G 45/40* (2013.01); *C07C 2523/44* (2013.01); *C10G 45/32* (2013.01)
USPC ........... 585/273; 585/250; 585/258; 585/259; 585/260; 585/271

(58) Field of Classification Search
CPC .............. C07C 5/00; C07C 5/02; C07C 5/23; C07C 5/25
USPC .................. 585/273, 250, 258, 259, 260, 271
See application file for complete search history.

(56) References Cited

U.S. PATENT DOCUMENTS

| | | | |
|---|---|---|---|
| 7,045,670 B2 * | 5/2006 | Johnson et al. ............... | 585/259 |
| 7,115,790 B2 | 10/2006 | Beller et al. | |
| 7,342,144 B2 | 3/2008 | Kaizik et al. | |
| 7,354,883 B2 | 4/2008 | Kaizik et al. | |
| 7,361,714 B2 | 4/2008 | Grass et al. | |
| 7,371,909 B2 | 5/2008 | Beller et al. | |
| 7,462,745 B2 | 12/2008 | Nierlich et al. | |
| 7,524,997 B2 | 4/2009 | Kaizik et al. | |
| 7,910,786 B2 | 3/2011 | Winterberg et al. | |
| 7,919,662 B2 | 4/2011 | Winterberg et al. | |
| 7,968,758 B2 | 6/2011 | Winterberg et al. | |
| 8,143,468 B2 | 3/2012 | Kaizik et al. | |
| 2001/0001805 A1 * | 5/2001 | Brown et al. ................. | 585/259 |
| 2002/0002315 A1 | 1/2002 | Kelly et al. | |
| 2002/0107424 A1 * | 8/2002 | Cheung et al. ............... | 585/275 |
| 2006/0025641 A1 | 2/2006 | Gartside et al. | |
| 2006/0041167 A1 | 2/2006 | Grass et al. | |
| 2007/0135665 A1 | 6/2007 | Wiese et al. | |
| 2008/0073250 A1 | 3/2008 | Bakshi | |
| 2009/0030250 A1 * | 1/2009 | Hill et al. ...................... | 585/273 |
| 2011/0118523 A1 | 5/2011 | Winterberg et al. | |
| 2012/0136186 A1 | 5/2012 | Lueken et al. | |
| 2012/0142985 A1 | 6/2012 | Winterberg et al. | |
| 2013/0030233 A1 | 1/2013 | Boeing et al. | |

FOREIGN PATENT DOCUMENTS

WO     2006 019717     2/2006

OTHER PUBLICATIONS

International Search Report Issued Sep. 5, 2011 in PCT/EP11/59601 Filed Jun. 9, 2011.
U.S. Appl. No. 14/009,722, filed Oct. 3, 2013, Maschmeyer.

* cited by examiner

*Primary Examiner* — In Suk Bullock
*Assistant Examiner* — Philip Louie
(74) *Attorney, Agent, or Firm* — Oblon, Spivak, McClelland, Maier & Neustadt, L.L.P.

(57) ABSTRACT

The present invention describes a process for the parallel selective hydrogenation of branched and unbranched multiply unsaturated $C_4$-$C_6$-hydrocarbons in olefin-containing hydrocarbon mixtures with minimization of hydrogenation and isomerization of the olefins present in the stream.

11 Claims, No Drawings

PROCESS FOR THE SELECTIVE HYDROGENATION OF MULTIPLY UNSATURATED HYDROCARBONS IN OLEFIN-CONTAINING HYDROCARBON MIXTURES

The present invention describes a process for the parallel selective hydrogenation of branched and unbranched multiply unsaturated $C_4$-$C_6$-hydrocarbons in olefin-containing hydrocarbon mixtures with minimization of hydrogenation and isomerization of the olefins present in the stream.

Industrial $C_4$-$C_6$-hydrocarbon mixtures from catalytic crackers or steam crackers usually contain not only saturated and monounsaturated compounds but also multiply unsaturated compounds. Before individual compounds can be isolated from these mixtures, it is frequently necessary to remove other compounds as completely as possible. This can be effected by physical methods such as distillation, extractive distillation or extraction and also by means of a selective chemical reaction of the components to be removed.

$C_4$ streams from steam crackers or catalytic crackers can, for example, have the following composition:

| Component | Proportion by mass/% |
|---|---|
| 1,3-Butadiene | 42 |
| Isobutene | 25 |
| 1-Butene | 16 |
| cis-2-Butene | 4 |
| trans-2-Butene | 5 |
| n-Butane | 5 |
| Isobutane | 2 |
| Acetylenes | 0.9 |
| C5+ | 0.1 |

The work-up of this mixture can, in one variant, be carried out by firstly reducing the concentration of 1,3-butadiene by means of extractive distillation or by means of a selective hydrogenation process for high butadiene concentrations to a value of about 1%. At the same time, the acetylenes present in the mixture are removed or converted into monounsaturated/saturated compounds. The $C_4$ mixture is referred to as raffinate 1 by those skilled in the art. In the next step, isobutene is removed, e.g. by converting it by means of methanol into methyl tert-butyl ether (MTBE) and removing the latter by distillation. If pure isobutene is to be isolated, the methyl tert-butyl ether can subsequently be cleaved to form isobutene and methanol again.

For the further work-up of the $C_4$ mixture, now raffinate 2, the multiply unsaturated compounds still remaining have to be converted by means of a selective hydrogenation process into the corresponding monounsaturated and saturated compounds. Now, 1-butene and isobutene can be separated off in sufficient purity by distillation and the remaining 2-butenes and the n-butane can be worked up further. The 2-butenes are frequently converted by dimerization into octenes which are subsequently converted by means of hydroformylation into PVC plasticizer alcohols. The saturated $C_4$-hydrocarbons can, for example, be used as blowing agents.

If the concentration of the multiply unsaturated compound is not reduced to a value of less than 10 ppm before the 1-butene is separated off in the selective hydrogenation process, the purity requirements for 1-butene used in polymerizations are not met. Furthermore, multiply unsaturated compounds reduce the catalytic activity of these catalysts for the dimerization of the 2-butenes.

The work-up of $C_4$ streams from steam crackers or catalytic crackers is described in principle in K.-D. Wiese, F. Nierlich, *DGMK-Tagungsbericht* 2004-3, ISBN 3-936418-23-3.

The selectivities in the processes for selective hydrogenation of multiply unsaturated hydrocarbons have to meet particularly demanding requirements since products of value are destroyed in the event of overhydrogenation, i.e. the hydrogenation of monounsaturated compounds, and also isomerization of terminal double bonds to internal double bonds. At the same time, the concentrations of multiply unsaturated compounds have to be reduced to values of usually <10 in the case of streams having high contents of multiply unsaturated compounds and to <10 ppm in the fine purification of streams which already have a low content of multiply unsaturated compounds.

Processes and catalysts for the selective hydrogenation of 1,3-butadiene in high concentration (~30-50%) in $C_4$ streams are described in EP 0 523 482, DE 31 19 850, EP 0 992 284 and EP 780 155.

$C_4$ streams can contain branched multiply unsaturated compounds having more than 4 carbon atoms, e.g. isoprene, in addition to unbranched multiply unsaturated compounds such as 1,3-butadiene. The presence of branched multiply unsaturated compounds is undesirable in the work-up of $C_4$ streams or interferes in this work-up for a number of reasons:

a) If branched multiply unsaturated compounds (e.g. isoprene) are present in the feed to the MTBE synthesis, these react with methanol to form the corresponding methyl ethers (e.g. 3-methoxy-3-methylbut-1-ene). If the MTBE is subsequently cleaved again, the branched multiply unsaturated compounds can reappear in the product and endanger its purity.

b) If the branched multiply unsaturated compounds get into the feed to the oligomerization of the n-butenes, they deactivate the oligomerization catalyst.

The selective hydrogenation of both the unbranched and branched multiply unsaturated compounds could overcome these problems in the work-up of $C_4$ streams. Thus, in the presence of unbranched and branched multiply unsaturated hydrocarbons, a process for the selective hydrogenation of unbranched multiply unsaturated $C_4$-hydrocarbons and a selective hydrogenation process for the hydrogenation of branched multiply unsaturated $C_5$-hydrocarbons would follow one another in order to reduce the concentration of both the branched and unbranched multiply unsaturated $C_4$- and $C_5$-hydrocarbons to values of <10 ppm.

EP 0 081 041 describes a process for the selective hydrogenation of multiply unsaturated or acetylenic compounds in low concentrations (<21%, preferably <1%) in $C_4$ streams. The process is carried out in a purely liquid phase and palladium on an inert support, e.g. aluminium oxide, serves as catalyst. To suppress the unwanted hydrogenation of monounsaturated compounds, carbon monoxide is added in an amount of from 0.05 to 20 ppm.

A process for the selective hydrogenation of branched multiply unsaturated $C_5$-hydrocarbons in $C_5$-hydrocarbon mixtures is described in EP 0 556 025.

In Alves et al., *Chem. Eng. J.* 2004, 99, 45, it is stated that 1,3-butadiene can be hydrogenated in a $C_4$ stream in the presence of isoprene to concentration values of <10 ppm, but the isoprene concentration is not reduced to similarly low values.

A person skilled in the art would therefore not expect unbranched multiply unsaturated $C_4$-hydrocarbons and branched multiply unsaturated $C_5$-hydrocarbons to be removed together to concentrations of <10 ppm in one process without a significant loss of monounsaturated hydrocarbons occurring or significant isomerization of α-olefins to internal olefins taking place because of the different reaction rates and the different adsorption constants of these groups of hydrocarbons (cf. Alves et al., *Chem. Eng. J.* 2004, 99, 45).

It was therefore an object of the invention to develop a process for the selective hydrogenation of unbranched multiply unsaturated $C_4$-hydrocarbons in low concentration in $C_4$-hydrocarbon mixtures, which likewise hydrogenates branched multiply unsaturated $C_5$-hydrocarbons present in the feed stream without the abovementioned undesirable secondary reactions occurring.

Contrary to the expectations of a person skilled in the art, it has been shown according to the present invention that unbranched multiply unsaturated $C_4$-hydrocarbons and branched multiply unsaturated $C_5$-hydrocarbons which occur as constituents in a $C_4$-hydrocarbon stream can be hydrogenated to concentration values of <10 ppm in one process. Here, the undesirable hydrogenation of the monounsaturated butenes which are likewise present in the feed stream and the isomerization of 1-butene occur to only a very minor extent.

The present invention accordingly provides a process for the selective hydrogenation of unbranched, multiply unsaturated $C_4$-hydrocarbons and branched, multiply unsaturated $C_5$-hydrocarbons in hydrocarbon mixtures with addition of hydrogen and carbon monoxide and using heterogeneous hydrogenation catalysts in a hydrogenation reactor, wherein the ratio of the volume of the feed stream into the hydrogenation reactor to the volume of the hydrogenation catalyst per hour of residence time is not more than 30 l/lh.

For the purposes of the present invention, unbranched, multiply unsaturated $C_4$-hydrocarbons are, in particular, 1,3-butadiene, but-3-en-1-yne and 1,2-butadiene.

For the purposes of the present invention, branched, multiply unsaturated $C_5$-hydrocarbons are, in particular, isoprene, 2-methylbut-1-en-3-yne, 2-methylbuta-1,2-diene, pent-4-en-2-yne and 3-methylbut-3-en-1-yne.

The ratio of the volume of the feed stream into the hydrogenation reactor to the volume of the hydrogenation catalyst per hour of residence time $[V_{feed}/(V_{cat}*RET)$, where RET=residence time] is important to the process of the invention and the success of the selective hydrogenation. This parameter is known to those skilled in the art as LHSV (liquid hourly space velocity). The volumes mentioned are in liters.

For the purposes of the present invention, the term "feed stream" refers to the totality of all liquid or gaseous reaction components which are fed into the hydrogenation reactor. These are, in particular, the hydrocarbon mixtures in which, inter alia, the unbranched, multiply unsaturated $C_4$-hydrocarbons and branched, multiply unsaturated $C_5$-hydrocarbons are present but also hydrogen and carbon monoxide.

According to the present invention, the LHSV to be adhered to is not more than 30 l/lh, in particular from 10 l/lh to 25 l/lh.

Only when the precise limits to the LHSV are adhered to can unbranched multiply unsaturated $C_4$-hydrocarbons and branched multiply unsaturated $C_5$-hydrocarbons which occur as constituents in a $C_4$-hydrocarbon stream be hydrogenated to concentration values of <10 ppm in one process without appreciable hydrogenation of the monounsaturated butenes which are likewise present in the feed stream and isomerization of 1-butene occurring. The proportion of unbranched multiply unsaturated $C_4$-hydrocarbons and branched multiply unsaturated $C_5$-hydrocarbons is, in particular, reduced to less than 10 ppm by the process of the invention.

The process of the invention is operated as a liquid-phase process, i.e. the reaction components are present in the liquid phase over the catalyst or are introduced in the liquid phase into the hydrogenation reactor.

The addition of hydrogen to the hydrocarbon mixture to be hydrogenated is thus effected in finely divided form and in such amounts that a homogeneous liquid phase is always present before entry into the hydrogenation reactor. The stoichiometric ratio (molar ratio) of hydrogen to the hydrocarbons to be hydrogenated is in the range from 2 to 1. The ratio is preferably in the range from 1.5 to 1. It is particularly preferably in the range from 1.2 to 1.

Carbon monoxide is additionally added to the hydrocarbon mixture to be hydrogenated. The content of carbon monoxide in the feed stream is in the range from 0.05 to 20 ppm of carbon monoxide, based on the mass of the hydrocarbon mixture. Preference is given to adding from 0.5 to 5 ppm of carbon monoxide. Amounts above 20 ppm no longer improve the hydrogenation results.

Heterogeneous hydrogenation catalysts are used as catalysts in the process of the invention. In particular, the hydrogenation catalysts are catalysts based on palladium, but the process of the invention is not tied to any particular palladium catalyst. The palladium is preferably present in supported form on an inert support material. The support material is, for example, aluminium oxide, silica gel or activated carbon. Preference is given to using aluminium oxide as support material. The catalyst has a palladium concentration which is in the range from 0.01 to 3%, based on the mass of the support. It is preferably in the range from 0.1 to 1%, very particularly preferably in the range from 0.3 to 0.5%. The catalyst has a BET surface area (determined by gas adsorption in accordance with DIN ISO 9277) of from 50 to 400 $m^2/g$, preferably from 100 to 300 $m^2/g$, particularly preferably from 200 to 300 $m^2/g$.

The temperature at which the feed stream enters the hydrogenation reactor is usually in the range from 0 to 100° C., preferably in the range from 20 to 80° C., particularly preferably in the range from 30 to 60° C. The pressure is usually in the range from 2 to 50 bar, preferably in the range from 6 to 30 bar, particularly preferably in the range from 10 to 25 bar.

The hydrogenation can be carried out in one or more reaction stages. If the amount of multiply unsaturated hydrocarbons present in the feed stream is so large that the necessary stoichiometric amount of hydrogen is no longer soluble in the feed stream, the feed stream can be diluted by means of the recycle mode. The hydrocarbon mixtures to be hydrogenated can contain up to 20% of multiply unsaturated hydrocarbons.

Even without further explanations, it is assumed that a person skilled in the art can utilize the above description in its widest scope. The preferred embodiments and examples are therefore merely to be interpreted as a descriptive disclosure which is not limiting in any way.

The present invention is illustrated below with the aid of examples.

Alternative embodiments of the present invention can be derived in an analogous way.

EXAMPLES

The hydrogenation is carried out in a fixed-bed reactor provided with a heating jacket through which a heat transfer oil (Marlotherm SH from Sasol Olefins & Surfactants GmbH) flows. 0.54 liter of a coated catalyst containing 0.5% of palladium on γ-aluminium oxide in extrudate form is used as catalyst. The specific internal surface area of the catalyst is about 250 $m^2/g$ and the pore volume is about 0.8 $cm^3/g$. The thickness of the palladium layer is about 0.05 mm. To produce the hydrocarbon mixture to be hydrogenated, raffinate 1, 1,3-butadiene and isoprene are mixed. Starting mixture and product mixture are analysed by gas chromatography.

Example 1

According to the Invention

| Component | 1,3-Butadiene | Isoprene | 1-Butene | Isobutane + balance | 2-Butene | C5-monoenes | n-butane |
|---|---|---|---|---|---|---|---|
| Feed [% by wt] | 0.2083 | 0.2451 | 28.8933 | 47.9032 | 13.4133 | 0 | 9.3368 |
| Output [% by wt] | 0.0006 | 0.0009 | 28.3557 | 47.7165 | 14.0890 | 0.2310 | 9.6063 |

| Reaction conditions | | | | | |
|---|---|---|---|---|---|
| T [° C.] | P [bar] | LHSV/ l/(l * h) | Ratio of $n(H_2)/n(diene)$ | CO concentration [ppm] | Conversion of 1-butene |
| 30 | 20 | 15 | 1.1 | 1.3 | 1.8% |

Example 2

Comparative Example

| Component | 1,3-Butadiene | Isoprene | 1-Butene | Isobutene + balance | 2-Butene | C5-monoenes | n-butane |
|---|---|---|---|---|---|---|---|
| Feed [% by wt] | 0.2403 | 0.2374 | 29.5211 | 47.7619 | 12.9960 | 0 | 9.2433 |
| Output [% by wt] | 0.0004 | 0.0220 | 29.3735 | 47.7233 | 13.1949 | 0.2171 | 9.4688 |

| Reaction conditions | | | | | |
|---|---|---|---|---|---|
| T [° C.] | P [bar] | LHSV/ l/(l * h) | Ratio of $n(H_2)/n(diene)$ | CO concentration [ppm] | Conversion of 1-butene |
| 30 | 20 | 36 | 1.1 | 1.0 | 0.5% |

Example 3

According to the Invention

| Component | 1,3-Butadiene | Isoprene | 1-Butene | Isobutane + balance | 2-Butene | C5-monoenes | n-butane |
|---|---|---|---|---|---|---|---|
| Feed [% by wt] | 0.1936 | 0.2421 | 29.5211 | 43.2569 | 13.1741 | 0 | 13.6122 |
| Output [% by wt] | 0.0006 | 0.0010 | 29.2902 | 43.2533 | 13.5940 | 0.2408 | 13.6201 |

| Reaction conditions | | | | | |
|---|---|---|---|---|---|
| T [° C.] | P [bar] | LHSV/ l/(l * h) | Ratio of $n(H_2)/n(diene)$ | CO concentration [ppm] | Conversion of 1-butene |
| 40 | 20 | 16 | 1.1 | 1.3 | 0.78% |

Example 4
According to the Invention

| Component | 1,3-Butadiene | Isoprene | 1-Butene | Isobutene + balance | 2-Butene | C5-monoenes | n-butane |
|---|---|---|---|---|---|---|---|
| Feed [% by wt] | 0.0956 | 0.2419 | 28.5082 | 43.9973 | 12.0909 | 0 | 15.0648 |
| Output [% by wt] | 0.0006 | 0.0010 | 27.9097 | 43.9966 | 12.7672 | 0.2557 | 15.0692 |

| Reaction conditions | | | | | |
|---|---|---|---|---|---|
| T [° C.] | P [bar] | LHSV/ l/(l * h) | Ratio of n(H$_2$)/n(diene) | CO concentration [ppm] | Conversion of 1-butene |
| 40 | 20 | 16 | 1.5 | 1.3 | 2.1% |

The tables in the examples in each case show the composition of the feed stream and of the output stream of the fixed-bed reactor under various reaction conditions. Example 1 shows the results of the hydrogenation of about 2000 ppm of 1,3-butadiene and about 2400 ppm of isoprene at an LHSV according to the invention. It can be seen that both 1,3-butadiene and isoprene can be hydrogenated to a proportion by mass of less than 10 ppm without large proportions of the products of value 1-butene and 2-butene being lost. 1-Butene is converted to an extent of only 1.8% (conversion=$(m_{in} - m_{out})/m_{in}$).

In Example 2, an LHSV of 36 l/(l*h) analogous to EP 0 081 041 is set. Here too, about 2000 ppm of 1,3-butadiene and about 2400 ppm of isoprene are present in the feed stream. However, at this high LHSV, the proportion by mass of isoprene is reduced only to a value of about 200 ppm, which is not acceptable in the fine purification of C$_4$ fractions.

In Example 3, the temperature is increased to 40° C. Here too, about 2000 ppm of 1,3-butadiene and about 2300 ppm of isoprene can be hydrogenated to a proportion by mass of less than 10 ppm without large proportions of the products of value being lost. 1-Butene is converted to an extent of 0.78%, while 2-butene again displays a negative conversion. The proportion of butanes as an indication of total hydrogenation likewise increases only by a value of less than 100 ppm.

In Example 4, the concentration of 1,3-butadiene is reduced to about 1000 ppm and at the same time the ratio of hydrogen to diene is increased from 1.1 to 1.5. Here too, about 2000 ppm of 1,3-butadiene and about 2300 ppm of isoprene can be hydrogenated to a proportion by mass of less than 10 ppm without large proportions of the products of value being lost. As a result of the increased hydrogen/diene ratio, 2.1% of 1-butene are now converted, but this is still a very low value. The conversion of 2-butene at the same time becomes more negative, which indicates increased isomerization of 1-butene to 2-butene. However, total hydrogenation to butanes takes place to only an insignificant extent.

The invention claimed is:

1. A process, comprising:
   selectively hydrogenating an unbranched, multiply unsaturated C$_4$-hydrocarbon and a branched, multiply unsaturated C$_5$-hydrocarbon in a hydrocarbon mixture with addition of hydrogen and carbon monoxide in the presence of a heterogeneous hydrogenation catalyst in a hydrogenation reactor,
   wherein a ratio of the volume of a feed stream comprising the hydrocarbon mixture, hydrogen, and carbon monoxide into the hydrogenation reactor to the volume of the hydrogenation catalyst per hour of residence time is from 10 to 25 l/h,
   wherein a temperature at which the feed stream enters the hydrogenation reactor is from 30 to 60° C., and
   wherein a content of carbon monoxide in the feed stream is from 0.5 to 5 ppm, based on the mass of the hydrocarbon mixture.

2. The process of claim 1, wherein the heterogeneous hydrogenation catalyst is a palladium catalyst.

3. The process of claim 1, being a liquid-phase process.

4. The process of claim 2, wherein the palladium catalyst is a supported catalyst comprising palladium and a support material.

5. The process of claim 4, wherein the support material is aluminum oxide, silica gel, or activated carbon.

6. The process of claim 5, wherein a content of the palladium catalyst is from 0.01 to 3%, based on a mass of the support material.

7. The process of claim 5, wherein a content of the palladium catalyst is from 0.1 to 1%, based on a mass of the support material.

8. The process of claim 5, wherein a content of the palladium catalyst is from 0.3 to 0.5%, based on a mass of the support material.

9. The process of claim 2, wherein the palladium catalyst has a BET surface area of from 50 to 400 m$^2$/g, determined by gas adsorption in accordance with DIN ISO 9277.

10. The process of claim 2, wherein the palladium catalyst has a BET surface area of from 100 to 300 m$^2$/g, determined by gas adsorption in accordance with DIN ISO 9277.

11. The process of claim 2, wherein the palladium catalyst has a BET surface area of from 200 to 300 m$^2$/g, determined by gas adsorption in accordance with DIN ISO 9277.

* * * * *